United States Patent [19]

Pingleton et al.

[11] Patent Number: 5,275,609
[45] Date of Patent: Jan. 4, 1994

[54] SURGICAL CUTTING INSTRUMENT

[75] Inventors: Edward D. Pingleton; Paul G. Thomson, both of Fillmore, Ind.

[73] Assignee: Vance Products Incorporated, Spencer, Ind.

[21] Appl. No.: 790,583

[22] Filed: Nov. 8, 1991

Related U.S. Application Data

[63] Continuation-in-part of Ser. No. 543,679, Jun. 22, 1990, abandoned.

[51] Int. Cl.$^5$ .................................................. A61B 17/39
[52] U.S. Cl. ..................................... 606/170; 606/167; 604/22; 128/753
[58] Field of Search ......................... 606/167–; 128/751–; 30/276, 347, 29.5; 604/22

[56] References Cited

U.S. PATENT DOCUMENTS

| | | | |
|---|---|---|---|
| 2,801,465 | 8/1957 | Cason | 30/29.5 |
| 3,381,373 | 5/1968 | Brown | 30/29.5 |
| 4,142,517 | 3/1979 | Stavropoulus | 128/754 |
| 4,368,734 | 1/1983 | Banko | 606/179 |
| 4,754,755 | 7/1988 | Hosted | 606/159 |

Primary Examiner—C. Fred Rosenbaum
Assistant Examiner—Manuel Mendez
Attorney, Agent, or Firm—Richard J. Godlewski

[57] ABSTRACT

A surgical cutting instrument is disclosed for percutaneously debulking tissue through an access sheath commonly used in minimally invasive laparoscopic or endoscopic surgical procedures. The cutting instrument includes a inner rotary member tube having a cutting edge at the distal end thereof for cutting and slicing tissue. The outside surface of the rotary inner cutting member tube and outer sheath annularly close about the distal ends thereof for preventing perforation of the surgical tissue bag in which the tissue is contained. The inner cutting member tube includes a hollow passageway for suctioning and aspirating tissue and fluid through the tube and into a collection chamber or out through a vacuum or suction line attached thereto. Vacuum or suction control ports are included at the proximal end of the inner cutting member tube and stationary sheath for also controlling the amount of vacuum or suction applied to the tissue. The surgical cutting instrument includes a control handle for grasping by the physician. A collection chamber is connected to a coupler connected to the stationary sheath for collecting tissue therein. The inner cutting member tube extends through the collection chamber to a drive motor or to a remotely positioned rotary drive mechanism. A vacuum line is attached to the collection chamber for drawing tissue and fluid through the inner cutting member tube and into the collection chamber.

20 Claims, 5 Drawing Sheets

SURGICAL CUTTING INSTRUMENT

CROSS-REFERENCE TO RELATED APPLICATION

This application is a continuation-in-part of application Ser. No. 07/543,679 filed Jun. 22, 1990, now abandoned, entitled "Surgical Cutting Instrument".

TECHNICAL FIELD

This invention relates to percutaneous surgical cutting instruments and, in particular, surgical instruments for debulking biological tissue.

BACKGROUND OF THE INVENTION

One of the major problems associated with minimally invasive surgery is percutaneously debulking or reducing a large tissue volume such as with a cyst, tumor, or an organ for removal through an access sheath. A number of power-driven, surgical cutting instruments are presently available in which a side port or a partial opening at the distal end of a cutting tube are rotated to shear and aspirate bone and cartilage through a lumen of the instrument. These side ports or partially open-ended cutting instruments are inefficient in debulking large volumes of soft tissue due to their limited access cutting surfaces, which require an angled or a side approach for cutting. Furthermore, these side port or partially open-ended instruments cannot core soft tissue. This significantly increases the time necessary to debulk and remove tissue through an access sheath. This is particularly applicable in laparoscopic or pelviscopic procedures in which large fibroid cysts must be removed. These power-driven side port or partially open-ended instruments are best suited for cutting cartilage or bone material in arthroscopic procedures, but are very inefficient in debulking and removing large volumes of soft tissue.

Another side port cutting instrument is manually operated and uses a series of opposing jaws that are opened and closed to grasp and shear the tissue. Such a manually-operated device is extremely limited in debulking tissue because of the time required for grasping and cutting each piece of the large tissue volume.

Another problem associated with these side port or partially open-ended instruments are the complex angles that are required for the cutting edges. Not only do these complex cutting angle instruments have limited access, but also provide limited control or directionality with respect to slicing or cutting soft tissue.

SUMMARY OF THE INVENTION

The foregoing problems are solved and a technical advantage is achieved by a surgical cutting instrument in which an open-ended rotary cutting edge positioned about the distal end of an inner elongated member extends beyond the distal end of a stationary outer sheath. The stationary sheath provides a protective guard for the inner member by limiting the lateral contact of the inner member with tissue, which advantageously prevents the wrapping of tissue around the inner rotary cutting member. The stationary sheath not only prevents tissue from wrapping around the rotary cutting member, but also prevents unwanted tearing or binding of the tissue around the inner cutting member. Wrapping tissue around the inner cutting member also severely limits the control and directionality of the cutting member through the tissue being debulked.

The rotary cutting edge extends circumferentially about the distal end of the inner member, thereby providing continual and head-on controlled cutting or debulking of the tissue. Such a configuration advantageously provides direct cutting or slicing of the tissue while maintaining precise control of the cutting operation.

The cutting edge of the inner rotating tube is radiused to cut soft tissue but yet not cut a surgical tissue bag, which may be brought in contact with the inner rotary cutting member.

Another outer safety shield is positioned about the inner cutting member and the stationary sheath and includes a rounded distal end, which further prevents puncturing of a tissue bag or unintended cutting of tissue. Laterally located about the distal end of the safety shield tube is an access channel through the passageway thereof for accepting tissue and guiding the tissue against the cutting edge of the inner rotary cutting member. This advantageously acts as a jaw for feeding the tissue into the cutting edge for cutting large portions of tissue. This variable size access channel also acts as a valve to control aspiration of fluid and tissue through the hollow passageway of the inner cutting member. Vacuum or suction control ports at the proximal end of the inner member and intermediately positioned stationary sheath also regulate the amount of vacuum or suction that is applied to the passageway of the inner cutting member for aspirating tissue or fluid therethrough.

The outer safety shield longitudinally slides along the stationary sheath to close and open the suction control ports of the inner member and the sheath for controlling the amount of vacuum or suction applied for aspirating tissue or fluid. The outer safety shield is also longitudinally extendable and withdrawable for controlling the size of the side access channel.

The outer shield includes a radial control arm attached to the proximal end of the shield for longitudinally sliding the shield with respect to the inner cutting member and stationary sheath and controlling the size of the side access channel and suction control ports.

The surgical cutting instrument also includes a collection chamber and an evacuation port for connecting a vacuum line thereto for aspirating tissue and fluid. The instrument further includes a rotary drive mechanism and coupler for rotating said inner member. A handle at the proximal end of the cutting instrument allows directional control of the instrument along with providing manual control of the instrument and the outer shield.

The foregoing problem of inadvertently cutting tissue with an open-ended surgical instrument is solved and a technical advantage is achieved by a surgical cutting instrument in which a cutting edge, that is positioned circumferentially about the distal end of an inner rotating member, is contained within the passageway of a stationary outer sheath. To further safeguard the cutting edge from inadvertent contact, the outer surface of the inner member and outer sheath annularly close about the distal ends thereof. The cutting action of the instrument is facilitated with a sideways motion when tissue is drawn through the distal ends of the outer sheath and inner member.

The distal ends of the elongated sheath and the inner member each have a distal opening therein. The hollow passageway of the elongated sheath has a first predetermined cross-sectional dimension, whereas the distal opening of the sheath has a second predetermined cross-sectional dimension smaller than that of the sheath passageway. The second distal opening of the inner member is positioned within the first opening of the elongated sheath and has a fourth predetermined cross-sectional dimension smaller than the third predetermined cross-sectional dimension of the inner member passageway.

Positioned between the inner member and elongated sheath is a bearing surface on which the inner member rotates freely within the passageway of the outer sheath. The bearing surface comprises an electrolyzed material such as chrome deposited on the outer surface of the inner member about the distal and proximal ends thereof. In another embodiment, the bearing surface comprises a tube of polytetrafluoroethylene that extends between the distal and proximal ends of the inner member.

To advantageously draw tissue into contact with the cutting edge that is circumferentially positioned about the distal end of the inner member, the cutting instrument includes suction means for drawing tissue through the first and second distal openings of the outer sheath and inner member. The inner member also includes an evacuation port communicating with the hollow passageway thereof and the suction means. A tissue collection chamber is also advantageously included in the instrument, which communicates with the evacuation port and suction means for collecting tissue received from the hollow passageway of the inner member.

The surgical cutting instrument also includes a rotary drive mechanism such as an electric motor connected to the proximal end of the inner member for rotating the member within the outer sheath. The annularly closing outer surface of the elongated sheath and inner member positioned about the distal ends thereof includes a uniformly radiused curvature for facilitating easy rotation of the inner member within the outer sheath and also for advantageously preventing inadvertent head-on cutting of tissue.

DETAILED DESCRIPTION

Figure 1:
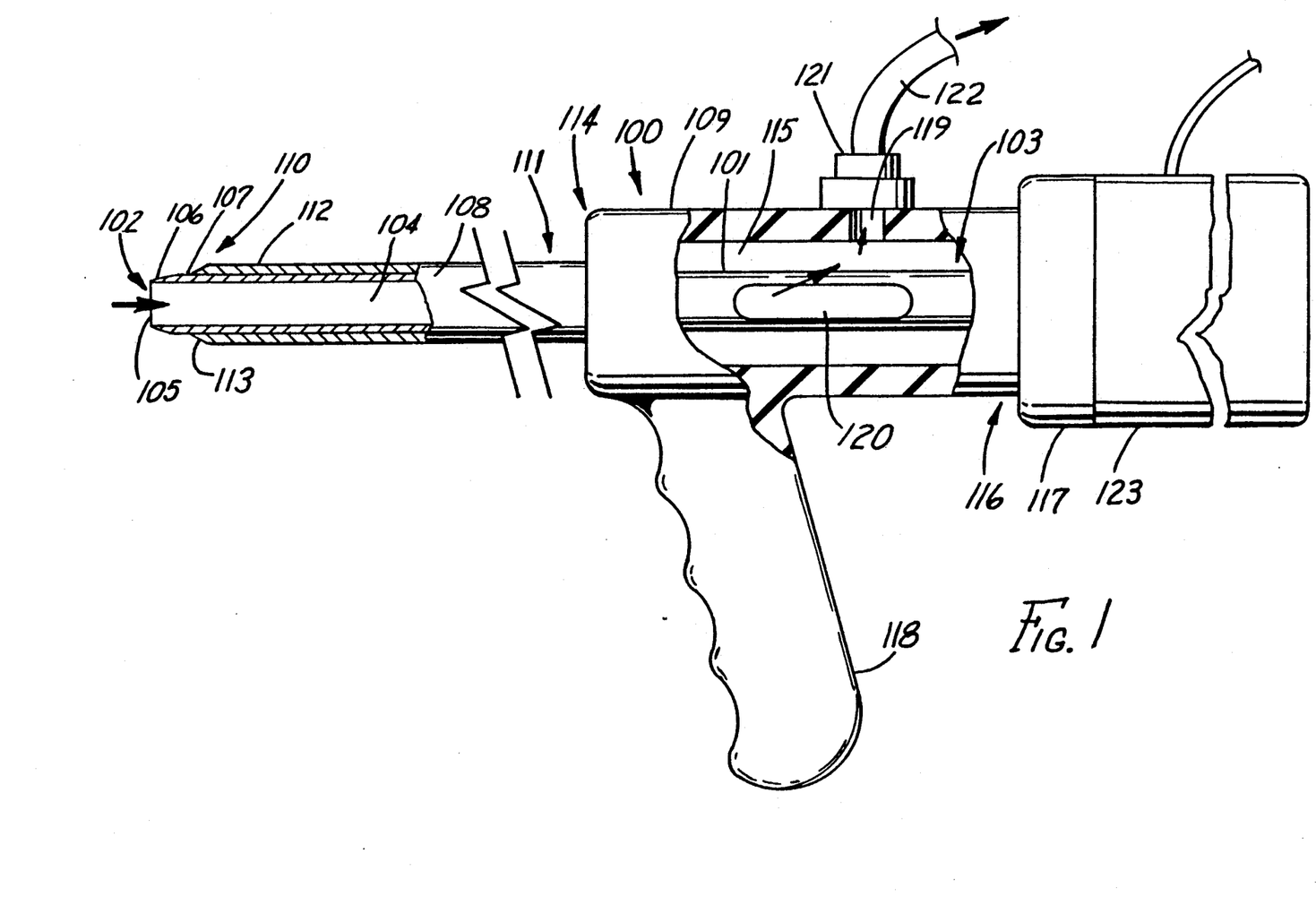
FIG. 1 depicts an illustrative surgical cutting instrument of the present invention.

Depicted in FIG. 1 is an illustrative surgical cutting instrument 100 for percutaneously debulking and cutting tissue through an access sheath that is commonly utilized in minimally invasive surgery. A trocar sheath is normally pushed through the skin and subcutaneous tissue layers into a cavity of the patient during, for example, an endoscopic or laparoscopic procedure. The cutting instrument is inserted through the sheath or into a percutaneously positioned surgical tissue bag for debulking or reducing large tissue volumes such as cysts, tumors, organs or the like. A preferred surgical tissue bag is disclosed in a U.S. patent application of one of the present inventors and filed concurrently herewith.

The cutting instrument comprises an inner elongated member tube 101 having a distal end 102, a proximal end 103, and a hollow passageway 104 extending longitudinally therebetween. Positioned at the distal end of the inner member tube is a rotary cutting edge 105 that is circumferentially positioned thereabout. The cutting edge includes radius 106 extending from the hollow passageway to an outer surface 107 of the inner member tube. The radiused edge reduces the possibility of puncturing a surgical tissue bag or unintentionally cutting tissue. Surrounding the rotary cutting tube is elongated stationary sheath 108 connected to coupler 109. The stationary sheath has a distal end 110, a proximal end 111, and a hollow passageway 112 positioned longitudinally therebetween. Distal end 112 includes a bevel 113 extending circumferentially therearound for preventing the tearing or ripping of tissue coming in contact therewith. By way of example, inner cutting member tube is a stainless steel tube having a 0.300" diameter with a wall thickness of 0.010". The stationary sheath is also a stainless steel tube having a 0.330" outside diameter with a 0.010" wall thickness. The lengths of the inner cutting member tube and the stationary sheath range in length preferably from 5-10 cm.

The proximal end 111 of stationary sheath 108 is connected to the distal end 114 of coupler 109. A hollow passageway 115 extends through the coupler to the proximal end 116 thereof where rotary drive mechanism 117 is connected thereto. By way of example, rotary drive mechanism 117 includes a well-known DC electric motor 123 connected to the proximal end 103 of rotary inner member tube 101. Alternatively, drive mechanism 123 may include a casing and well-known bearings for applying air to a turbine also positioned at the proximal end of the inner cutting member tube. Other well-known means of providing a rotary motion to the inner cutting member are also contemplated. A handle 118 extends radially from the coupler to provide manual control of the entire cutting instrument by the attending physician. An evacuation port 119 extends radially from hollow coupler passageway 115 for suctioning tissue and other fluid from side proximal evacuation port 120 of inner cutting member tube 101. A well-known connector 121 provides means for fastening a vacuum line or suction tube 122 to coupler 109.

As previously suggested, the inner cutting member tube extends through stationary sheath 108 with the proximal end 103 extending through the hollow passageway of the coupler for connection to rotary drive mechanism 117.

Figure 2:
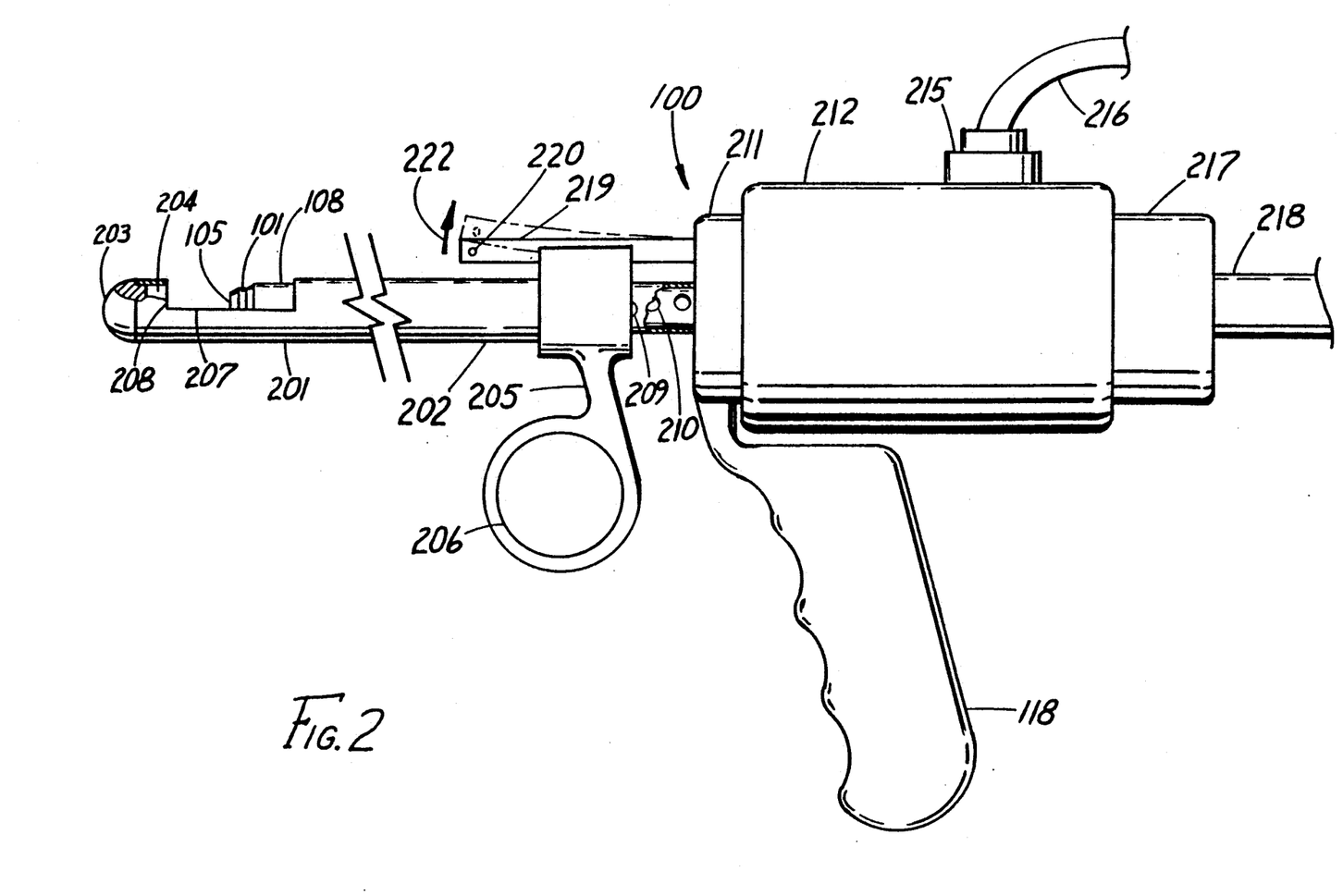
FIG. 2 depicts the surgical cutting instrument of FIG. 1 modified to receive an outer shield for containing the inner cutting member and stationary sheath of FIG. 1.
Figure 3:
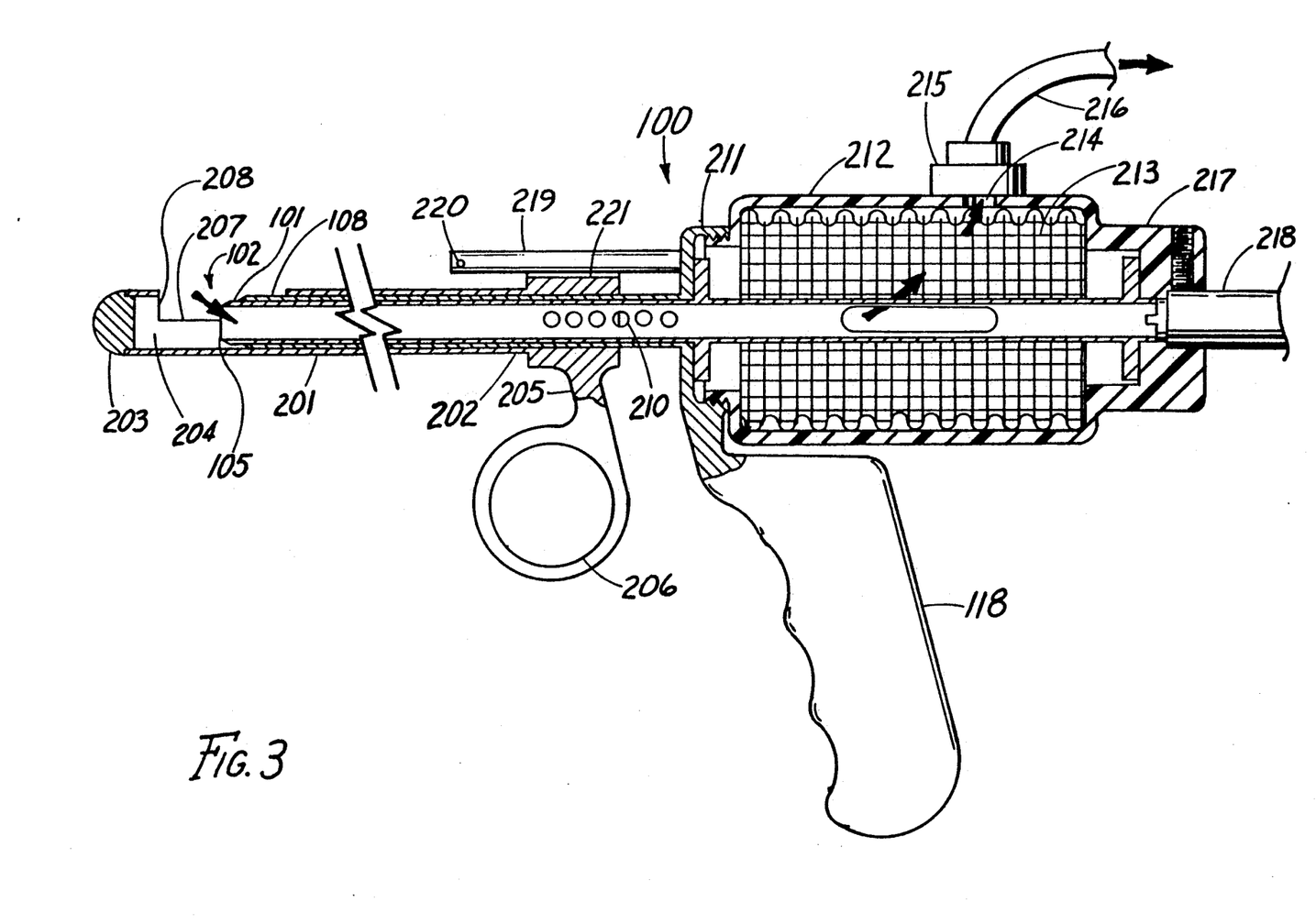
FIG. 3 is a cross-sectional view of the surgical cutting instrument of FIG. 2.

Depicted in FIG. 2 is a side view and in FIG. 3 a partial cross-sectional view of a modified embodiment of surgical cutting instrument 100 of FIG. 1 with an outer safety shield 201 positioned about stationary sheath 108 and inner cutting member tube 101. Outer safety shield 201 includes a proximal end 202, a rounded distal end 203, and a hollow passageway 204 positioned and extending longitudinally therebetween. The shield is sized for inserting the stationary sheath and the inner cutting member tube within passageway 204. By way of example, the outer shield comprises a stainless steel tube having a 0.340" outside diameter with a wall thickness of 0.015". The distal end 203 of the outer shield is rounded to prevent unintentional cutting of tissue and puncturing the surgical tissue bag should such be utilized in the surgical procedure.

Extending radially from the proximal end is a control arm 205 having an eyelet ring 206 at the proximal end thereof for slidably controlling the position of the outer shield with respect to stationary sheath 108 and inner cutting member tube 101. The attending physician typically inserts his index finger therein while the rest of the hand grasps control handle 118.

Positioned about the distal end 203 of the outer shield is access channel 207 that extends laterally across the shield tube and through hollow passageway 204. Face edge 208 of the channel acts as a jaw for grasping tissue and feeding it into cutting edge 105 of the inner cutting member tube. In this modified embodiment, distal end 102 of the inner cutting member tube is beveled to provide a sharper cutting edge 105. Control eyelet ring 206 is longitudinally moved by the physician to cause face edge 208 of the channel to engage and draw the tissue into the cutting edge of the inner cutting member tube.

A plurality of vacuum control ports 209 are positioned longitudinally along the length of stationary sheath 108. A plurality of vacuum access ports 210 are correspondingly positioned with respect to access port 209 of the stationary sheath to control the amount of vacuum applied to the distal end of the inner cutting member tube. As the outer shield 201 is longitudinally moved along stationary sheath 108, the vacuum control access ports are either opened or covered up to allow respectively more or less suction to be applied to the distal end of the inner cutting member tube.

As depicted in FIGS. 2 and 3, coupler 211 has been modified to receive a detachable tissue collection chamber 212. Handle 118 is fixedly attached to coupler 211 as is stationary sheath 108. The collection chamber is of a cylindrical form including a cylindrical collection screen 213 for collecting tissue as vacuum is applied via evacuation port 214, vacuum connector 215, and vacuum tube 216. Vacuum tube 216 is connected to a source of suctioning vacuum, which is readily available in most surgical suites. The inner cutting member tube extends longitudinally through the collection chamber to rotary drive mechanism 217 which is part of the proximal end of the collection chamber. The proximal end of the inner rotary cutting member tube is connected to a remote source of rotary power via rotary power line 218. Means for positioning the inner cutting member tube within, the collection chamber using two bearing flanges and a slotted end are well-known in the art and may be readily modified by one skilled in the art to accept any number of different types of rotary drive mechanisms. The rotary drive mechanism may include a remote source of power as indicated in this particular example or may be integrally incorporated into the cutting instrument as was described with respect to FIG. 1.

Extending longitudinally from coupler 211 is elongated stop arm 219 having a cross member 220 positioned at the distal end thereof. The built-up distal end of radial control arm 205 includes a longitudinal slot or channel 221 formed therein for slidably receiving stop arm 219. Cross member 220 limits the longitudinal motion of the outer shield when control arm 205 engages cross member 220. The distal end of the control arm is moveable as shown by arrow 222 to remove the outer shield for cleaning.

Figure 4:
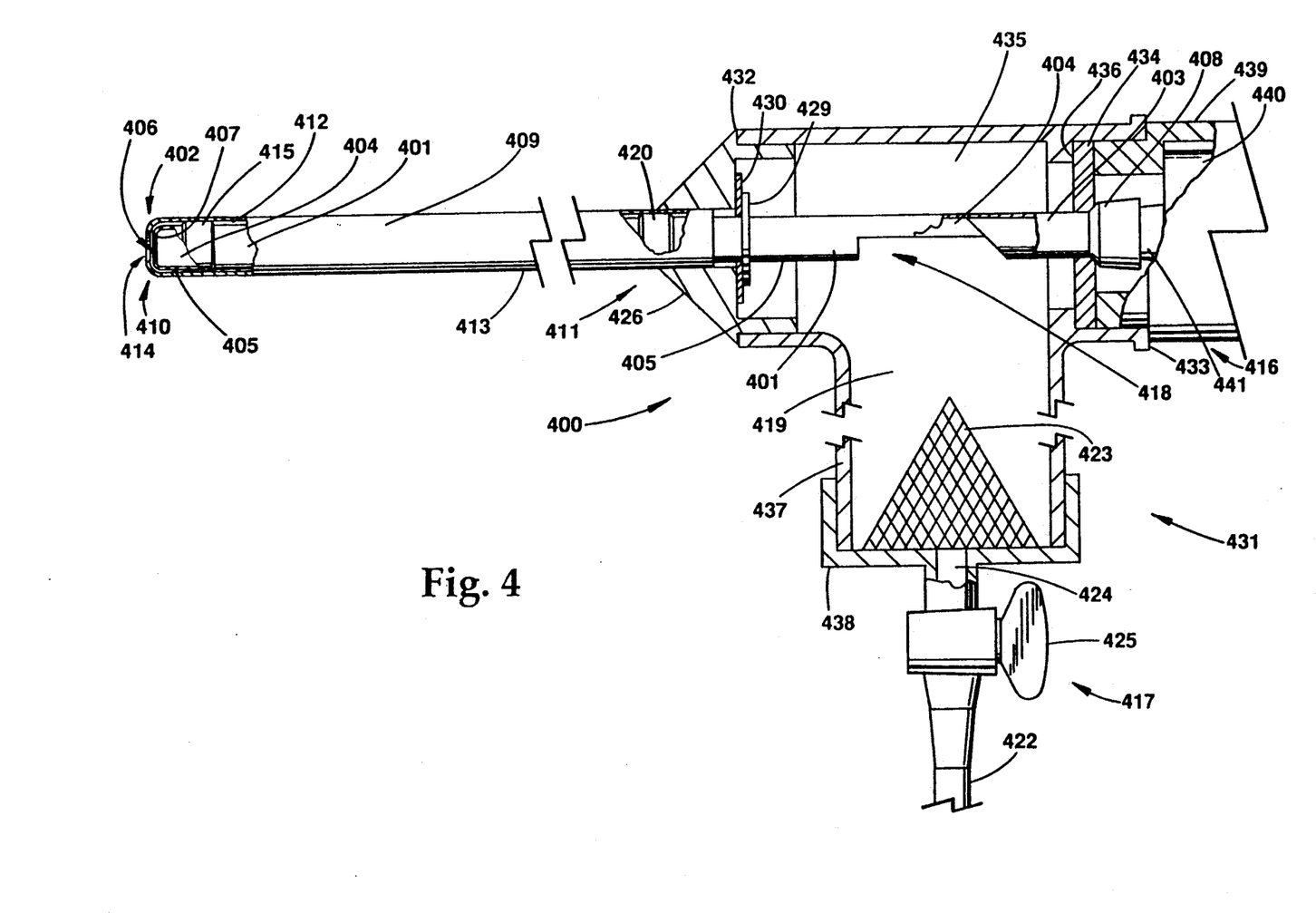
FIG. 4 depicts a partially sectioned side view of another embodiment of the surgical cutting instrument of the present invention.

Depicted in FIG. 4 is a partially sectioned side view of another illustrative surgical cutting instrument 400 having a rotary, open-ended cutting edge 407 for percutaneously debulking and cutting tissue. The cutting edge is completely contained within passageway 412 of outer sheath 409, which annularly closes about distal end 410 thereof to prevent perforation of the surgical tissue bag. The cutting instrument comprises an inner elongated cutting member tube 401 rotatably positioned within outer elongated sheath tube 409. Tissue is drawn into hollow passageway 404 of inner cutting tube member 401 with a vacuum applied thereto and cut with a sideways or lateral motion of the distal end of the instrument, which is provided by the attending physician. Rotary drive mechanism 416 includes, for example, electric motor 440, which is positioned about proximal end 403 of inner cutting member tube 401 for rotating the tube and cutting tissue drawn within. A suction or vacuum line 422 is connected to the handle of the instrument to draw tissue within hollow passageway 404 of the inner cutting member tube. Severed tissue is drawn through the inner cutting member tube and exits evacuation port 418 of the tube into tissue collection chamber 419, which is positioned in the handle of the instrument. Conically shaped screen 423 positioned in the bottom of the tissue collection chamber over vacuum port 424 prevents the severed tissue from exiting the chamber and blocking the vacuum line. Vacuum control means 417 includes stopcock 425 that is positioned between the vacuum port and vacuum line and controls the amount of suction or vacuum applied to the cutting instrument.

Inner cutting member tube 401 includes distal end 402, proximal end 403, and hollow passageway 404 extending longitudinally therein. Surrounding the rotary inner cutting member tube is stationary outer elongated sheath tube 409 with proximal end 411 thereof connected to the handle of the instrument via coupler 426. Hollow passageway 412 extends longitudinally in the outer sheath between distal end 410 and proximal end 411.

Figure 5:
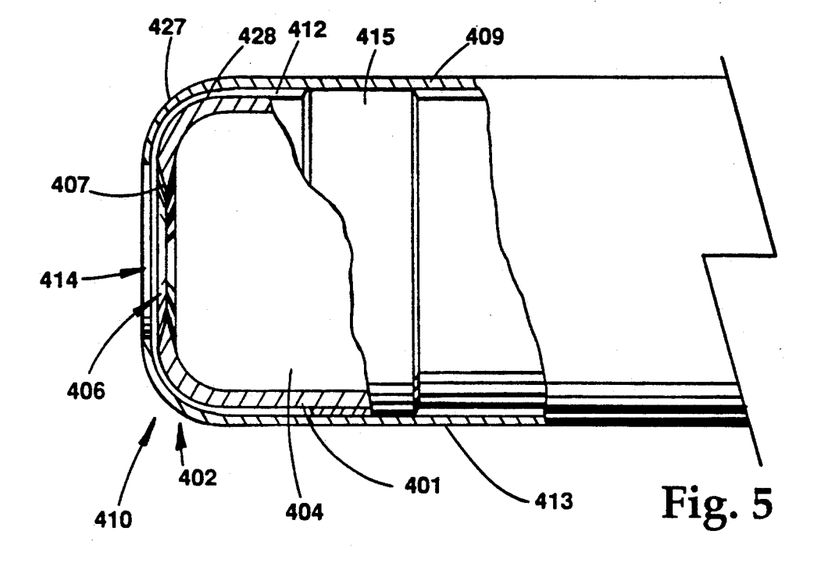
FIG. 5 depicts a partially sectioned side view of the distal end of the surgical cutting instrument of FIG. 4.
Figure 6:
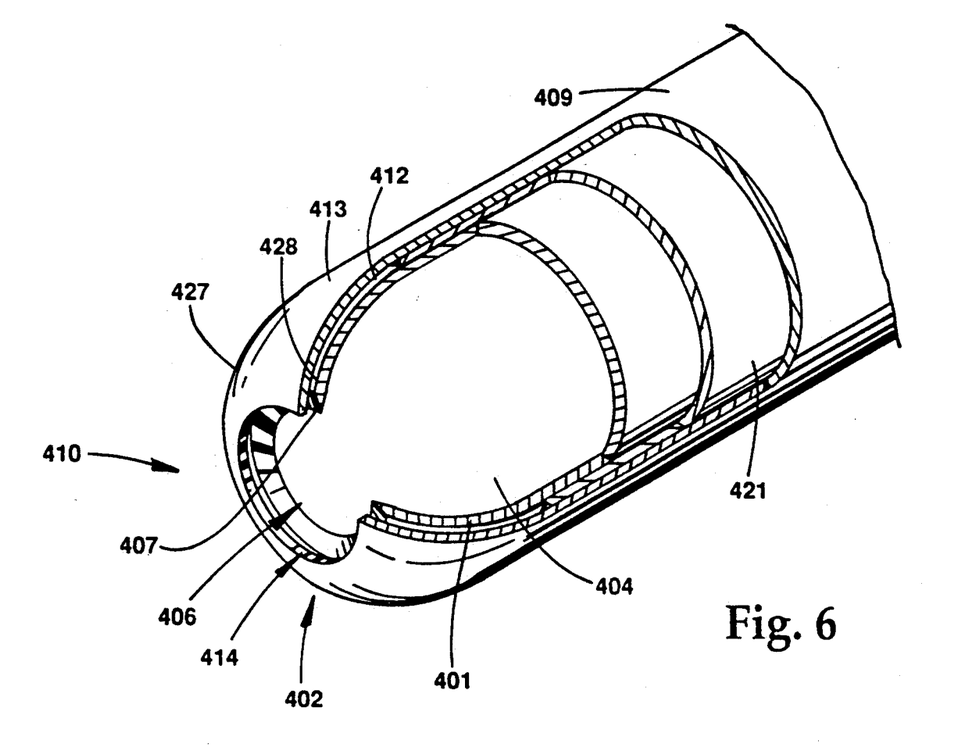
FIG. 6 depicts a partially sectioned pictorial view of the distal end of the surgical cutting instrument of FIG. 4.

Depicted in FIGS. 5 and 6 are enlarged partially sectioned views of distal end 402 of inner cutting member tube 401 and distal end 410 of outer sheath 409 of the cutting instrument. To prevent perforation of a surgical tissue bag of which the tissue is contained, outer surface 413 of the stationary outer sheath closes annularly about distal end 410. Tissue is drawn through distal opening 414 of the outer sheath for engagement with rotary cutting edge 407 that is circumferentially positioned about distal opening 406 of the rotary inner cutting member tube. The physician applies a sideways or circular motion to the distal end of the instrument for rotary edge 407 to cut the tissue drawn through the distal openings of the outer sheath and inner member tube. To further prevent perforation of the surgical tissue bag and ease operation of the instrument therein, respective annularly closing surfaces 427 and 428 of outer sheath 409 and inner cutting member tube 401 are uniformly radiused. As a result, distal opening 414 of the outer sheath and distal opening 406 of the inner cutting member tube each have a cross-sectional diameter dimension smaller than the cross-sectional diameter dimension of respective hollow passageways 412 and 404. In addition, circular distal opening 406 of the inner tube is positioned within distal opening 414 of the outer sheath and has a smaller cross-sectional diameter dimension to draw tissue into the inner cutting member tube and into contact with rotary cutting edge 407 to cut the tissue with a sideways or circular motion provided by the attending physician.

By way of example, outer elongated sheath tube 409 comprises a 300 series stainless steel tube approximately 4.875" in length with an outside diameter of 0.428" and inside diameter of 0.410". The diameter of distal opening 414 of the outer sheath is approximately 0.310" to 0.315" with outer annularly closing surface 427 having a uniform radius of approximately 0.100". Inner cutting member tube 401 comprises a 7.500" length of 300 series stainless steel tube having an outside diameter dimension of approximately 0.377" with a wall thickness of 0.010" resulting in an inside diameter of approximately 0.357". The diameter of circular distal opening 406 is approximately 0.275" with outer annularly closing surface 428 having a uniform radius of approximately 0.100". Rotary cutting edge 407 has an included angle of approximately 25 to 30 degrees and faces inwardly in a perpendicular radial direction toward the longitudinal axis of the cutting tube. This particular orientation provides for a sideways cutting or sculpting action when tissue is drawn with suction through distal openings 406 and 414. As partially depicted in FIG. 4, approximately 0.375" from proximal end 403 of the inner cutting member tube, evacuation port 418 extends for approximately 1.125" with a depth of 0.177" from outer surface 405 into hollow passageway 404. Nylon coupler 408 is fixedly positioned in hollow passageway 404 and extends from proximal end 403 of the inner cutting member tube for detachable engagement with shaft 441 of electric motor 440.

As depicted in FIGS. 4 and 5, positioned about distal end 402 on outer surface 405 of the inner member is distal bearing surface 415 approximately 0.5 cm in length and 0.5 cm from distal end 402. This bearing surface is approximately 0.015" in thickness and comprises an electrolyzed material such as 95% hard chrome for rotating inner member 401 within the passageway of the outer sheath. A proximal bearing surface 420 is similarly positioned on the outer surface of the inner member about the proximal end of the outer sheath. The distance between the distal end of the rotary inner cutting member tube and the stationary outer sheath is maintained with thrust disk 429, which is positioned around inner member tube 401 proximal to the outer sheath and engages distal handle coupler 426 and polytetrafluoroethylene bearing disk 430. Alternatively as shown in FIG. 6, a thin-wall tube 421 of approximately 0.015" polytetrafluoroethylene material is inserted between the inner member and outer sheath, which acts as the bearing surface.

Hollow passageway 404 of rotary inner cutting member tube 401 extends the entire length of the tube for drawing and removing tissue severed from the surgical site through tissue evacuation port 418 and into tissue collection chamber 419. Handle 431 of the instrument comprises a cylindrical T-shaped member with coupler 426 fixedly positioned in distal cross-bar opening 432. Rotary inner cutting member tube 401 is inserted through proximal cross-bar opening 433 of handle 431 and into outer sheath 409. A circular solimide material disk 434 is positioned about the proximal end of the cutting tube to prevent tissue from being drawn into electric motor 440. The disk is fixedly positioned in passageway 435 of the handle about proximal cross-bar opening 433 between inwardly extending flange 436 and the distal end of the rotary drive mechanism.

Tissue collection chamber 419 of the cutting instrument handle includes hollow T-shaped passageway 435 which communicates with inner passageway 404 of the rotary inner cutting member tube via evacuation port 418. The tissue collection chamber is enclosed by cylindrical wall 437 of the T-shaped handle. The proximal end of the chamber includes removable cap 438 with chamber evacuation port 424 positioned therein and vacuum stopcock 425 extending therefrom. As previously discussed, conically-shaped screen 423 prevents tissue from being drawn through evacuation port 424 and into vacuum or suction line 422. Suction means 417 of the cutting instrument comprises evacuation port 424, stopcock 425, and conically-shaped screen 423. The cylindrical T-shaped handle of the instrument is comprised of any well-known plastic material such as polyvinylchloride which is easily molded and shaped. Rotary drive mechanism 416 comprises a commercially available electrical motor 440 that is encased, for example, in plastic material cylinder case 439, which is readily screwed into proximal cross-bar opening 433 of the handle to engage rotary inner cutting member tube coupler 408.

With rotary drive mechanism 416 rotating inner cutting member tube 401, tissue is severed with cutting edge 407 and drawn through hollow passageway 404 and into tissue collection chamber 419 via evacuation port 418. A power and control line (not shown) is connected to the rotary drive mechanism to energize and control the speed of the electric motor. The physician controls the speed, for example, with the use of a foot pedal (not shown) connected to the power and control line. The vacuum applied to the tissue collection chamber via the suction means draws the severed tissue from the inner cutting member tube and into the collection chamber of the surgical cutting instrument handle. The physician regulates the suction applied to the chamber via stopcock 425.

It is to be understood that the above-described surgical cutting instrument is merely an illustrative embodiment of the principles of this invention and that other cutting instruments may be devised by those skilled in the art without departing from the spirit and scope of this invention. In particular, the distal end of the cutting instrument may be devised to include serrated teeth or a modified cutting edge for providing any number of different cutting or slicing actions. The rounded distal end of the outer shield may be devised to include a series of rounded wires to permit penetration through soft tissue to permit cutting and slicing by the inner cutting member tube. Such a wire cage arrangement would also prevent puncture of a surgical tissue bag should one be desired to be used by the physician.

What is claimed is:
1. A surgical cutting instrument comprising:
an elongated sheath having a first distal end including a first distal opening, a first proximal end, and a first hollow passageway positioned longitudinally therein, said sheath having a first outer surface annularly closing in a continuous manner about said first distal end, said first distal opening being uniform and of a smaller cross-sectional dimension than of said first hollow passageway; and
an inner elongated member rotatably positioned within said first hollow passageway of said sheath, said member having a second distal end contained within said first hollow passageway of said sheath, a second proximal end connectable to a rotary drive mechanism, and a second hollow passageway extending from said second distal end thereof for removing tissue, said inner member also having a second outer surface annularly closing about said second distal end thereof, said second distal end of said member including a second distal opening positioned within said first opening and having a cutting edge positioned circumferentially thereabout contained within said first hollow passageway at said first distal end for cutting through tissue when said member is rotated.

2. The instrument of claim 1 wherein said first hollow passageway has a first predetermined cross-sectional dimension, wherein said first distal opening has a second predetermined cross-sectional dimension smaller than said first predetermined dimension, wherein said second hollow passageway of said inner elongated member has a third predetermined cross-sectional dimension and wherein said second distal opening of said inner elongated member has a fourth predetermined cross-sectional dimension smaller than said third dimension.

3. The instrument of claim 2 wherein said fourth predetermined dimension of said second distal opening of said inner elongated member is smaller than said second predetermined cross-sectional dimension of said first distal opening of said outer sheath.

4. The instrument of claim 1 further comprising a bearing surface positioned between said inner member and said outer sheath.

5. The instrument of claim 4 wherein said bearing surface comprises an electrolyzed material deposited on said outer surface of said inner member about said second distal end thereof.

6. The instrument of claim 5 wherein said electrolyzed material comprises chrome.

7. The instrument of claim 1 further comprising said rotary drive mechanism.

8. The instrument of claim 7 wherein said rotary drive mechanism includes an electric motor.

9. The instrument of claim 1 further comprising suction means communicating with said second passageway of said inner member for drawing tissue through said first and second distal openings.

10. The instrument of claim 9 wherein said inner member includes an evacuation port positioned about said second proximal end thereof and communicating with said second passageway and said suction means.

11. The instrument of claim 10 further comprising a tissue collection chamber communicating with said evacuation port and said suction means for collecting tissue received from said second passageway therein.

12. The instrument of claim 1 wherein said outer surface closing about said first distal end of said outer sheath includes a first uniformly radiused, longitudinal curvature.

13. A surgical cutting instrument comprising:
an elongated sheath having a first distal end including a first distal opening, a first proximal end, and a first hollow passageway positioned longitudinally therein, said sheath having a first outer surface uniformly radiused longitudinally and annularly closing in a continuous manner about said first distal end, said first distal opening being uniform and of a smaller cross-sectional dimension than of said first hollow passageway; and
an inner elongated member rotatably positioned within said first hollow passageway of said sheath, said member having a second distal end contained within said first hollow passageway of said sheath, a second proximal end connectable to a rotary drive mechanism, and a second hollow passageway extending from said second distal end thereof for removing tissue, said inner member also having a second outer surface uniformly radiused longitudinally and annularly closing about said second distal end thereof, said second distal end of said member including a second distal opening positioned within said first opening and having a cutting edge positioned circumferentially thereabout and contained within said first hollow passage at said first distal end for cutting through tissue when said member is rotated.

14. The instrument of claim 13 further comprising suction means communicating with said second passageway of said inner member for drawing tissue through said first and second distal openings.

15. The instrument of claim 13 further comprising said rotary drive mechanism.

16. The instrument of claim 15 further comprising a bearing surface positioned between said inner member and said outer sheath.

17. The instrument of claim 16 wherein said bearing surface comprises polytetrafluoroethylene.

18. The instrument of claim 16 wherein said bearing surface comprises chrome.

19. The instrument of claim 14 further comprising a tissue collection chamber communicating with said second passageway of said inner member and said suction means for collecting tissue therein.

20. A surgical cutting instrument comprising:
an elongated sheath having a first distal end including a first distal opening, a first proximal end, and a first hollow passageway positioned longitudinally therein, said sheath having a first outer surface uniformly radiused longitudinally and annularly closing in a continuous manner about said first distal end, said first passageway having a first predetermined cross-sectional dimension, said first distal opening being uniform and having a second predetermined cross-sectional dimension smaller than said first predetermined dimension;
an inner elongated member rotatably positioned within said first hollow passageway of said sheath, said member having a second distal end completely contained within said first hollow passageway of said sheath, a second proximal end connectable to a rotary drive mechanism, and a second hollow passageway extending from said second distal end thereof for removing tissue, said inner member also having a second outer surface uniformly radiused longitudinally and annularly closing about said second distal end thereof, said second passageway having a third predetermined cross-sectional dimension, said second distal opening having a fourth predetermined cross-sectional dimension smaller than said second and third dimensions, said second distal end of said member including a second distal opening positioned within said first opening and having a cutting edge positioned circumferentially thereabout and contained within said first hollow passageway at said first distal end for cutting through tissue when said member is rotated, said inner member having an evacuation port positioned about said second proximal end and communicating with said second passageway;

a first bearing surface positioned on said outer surface of said inner member about said second distal end;

a second bearing surface positioned on said outer surface of said inner member about said second proximal end, said first and second bearing surfaces including chrome and positioned between said outer sheath and said inner member;

a tissue collection chamber communicating with said second hollow passageway of said inner member via said evacuation port;

suction means communicating with said tissue collection chamber and said second hollow passageway of said inner member for drawing tissue into said first and second distal openings; and a rotary drive mechanism connectable to said inner member for rotation thereof.

* * * * *